United States Patent [19]
Klaus et al.

[11] Patent Number: 5,990,329
[45] Date of Patent: Nov. 23, 1999

[54] RETINOIDS

[75] Inventors: Michael Klaus, Weil am Rhein, Germany; Peter Mohr, Basle, Switzerland

[73] Assignee: Hoffman-La Roche Inc., Nutley, N.J.

[21] Appl. No.: 08/832,493

[22] Filed: Apr. 3, 1997

[30] Foreign Application Priority Data

Apr. 15, 1996 [EP] European Pat. Off. ............. 96105849

[51] Int. Cl.⁶ ................................................ C07C 59/147
[52] U.S. Cl. ............................................ 554/118; 554/214
[58] Field of Search ...................................... 554/118, 214

[56] References Cited

U.S. PATENT DOCUMENTS 4,169,103 9/1979 Haenni et al. .

FOREIGN PATENT DOCUMENTS

| | | |
|---|---|---|
| 1143657 | 3/1983 | Canada . |
| 010 208A1 | 4/1980 | European Pat. Off. . |
| 552624 | 7/1993 | European Pat. Off. . |
| 35 09 455 A1 | 10/1985 | Germany . |
| 211 167 A9 | 6/1995 | Hungary . |
| 2156676 | 10/1985 | United Kingdom . |

OTHER PUBLICATIONS

Masayoshi Ito et al., Chem. Phar. Bull., vol. 36 (1), pp. 78–86 (1988).
Barua et al., Biochem. J., vol. 168:557–564 (1977).
Mayer et al., Helvetica Chemica Acta, vol. 63, Fasc. 6, Nr. 156, pp. 1467–1472 (1980).
Doran et al., Methods in Enzymology, 190:334–338 (1990).
Kistler, Arch. Toxiol., 60:403–414 (1987).
Widmeer, Pure & Appl. Chem., vol. 57, No. 5, pp. 741–752 (1985).
Curley et al., Pharmaceutical Research, vol. 7, No. 3, pp. 270–273 (1990).
CA 112:213684 (1990).
CA 110:231910 (1988).

*Primary Examiner*—Paul J. Killos
*Attorney, Agent, or Firm*—George W. Johnston; William H. Epstein

[57] ABSTRACT

Compounds of the formula:

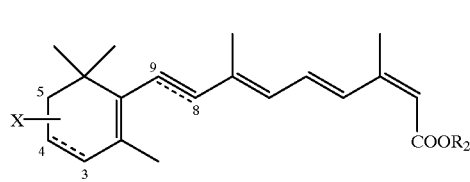

wherein $R^2$ and X are as described, are disclosed. The compounds are useful for treating dermatological disorders which are accompanied by epithelial lesions, e.g., acne and psoriasis, as well as malignant and premalignant epithelial lesions, tumours and precancerous changes of the mucous membrane in the mouth, tongue, larynx, oesophagus, bladder, cervix and colon.

18 Claims, No Drawings

RETINOIDS

SUMMARY OF THE INVENTION

The present invention is concerned with novel retinoids of the formula:

I wherein
X is oxo or a group $OR^1$ in the 4- or 5-position;
$R^1$ is hydrogen, alkyl or acyl; and
$R^2$ is hydrogen or alkyl;
the dotted bonds are optional and a 3,4-double bond can only be present when X is in the 5-position;
as well as pharmaceutically usable salts of carboxylic acids of formula I.

DETAILED DESCRIPTION OF THE INVENTION

The present invention is concerned with novel retinoids of the formula:

I wherein
X is oxo or a group $OR^1$ in the 4- or 5-position;
$R^1$ is hydrogen, alkyl or acyl; and
$R^2$ is hydrogen or alkyl;
the dotted bonds are optional and a 3,4-double bond can only be present when X is in the 5-position;
as well as pharmaceutically usable salts of carboxylic acids of formula I.

Furthermore, the invention is concerned with a process for the manufacture of these retinoids and their salts, pharmaceutical preparations containing these retinoids or their salts as well as the use of these retinoids and their salts as medicaments or for the production of medicaments.

In the compounds of the invention alkyl groups are preferably lower alkyl groups (with "lower" meaning groups with 1–7 carbon atoms), which can be straight-chain or branched, such as methyl, ethyl, propyl, isopropyl, butyl, isobutyl, tert.-butyl, pentyl, hexyl and heptyl. The term "acyl" means lower alkanoyl groups such as acetyl, propionyl, butyryl and pivaloyl; aromatic acyl groups such as benzoyl and toluyl; and araliphatic acyl groups such as phenylacetyl.

Compounds of the invention in which X is a group $OR^1$ can be R- or S-enantiomers or racemates (RS).

A preferred group of compounds of the invention are compounds of the formula:

IA especially those of the formulae:

where X is bonded at the 4 or 5 position on the ring, and

Particularly preferred are compounds of the formula:

IB especially those of the formula:

IC

Other examples of compounds of the invention are compounds of the formula:

ID

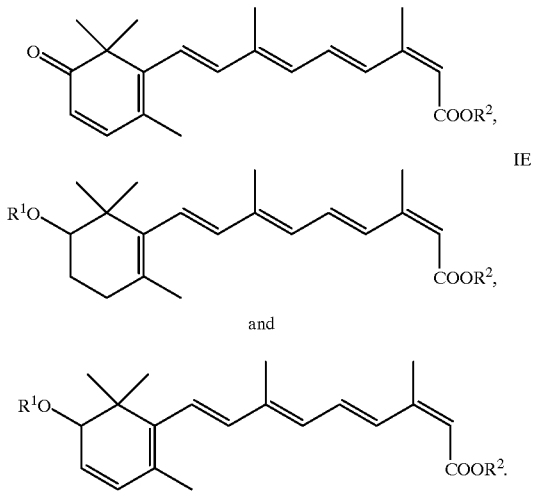

Of the compounds having a triple bond in the side-chain, the compounds of the formula:

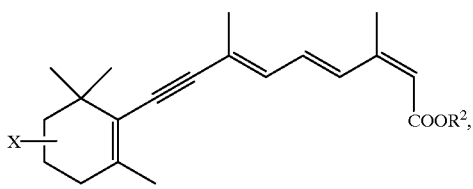

where X is bonded at the 4 or 5 position on the ring, are preferred, especially compounds of the formula:

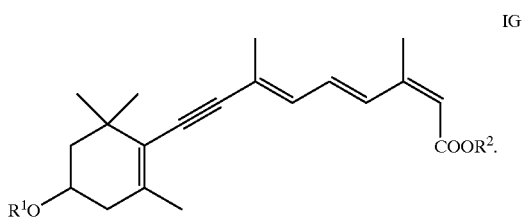

A further example of a compound of the invention with a triple bond in the side-chain is a compound of the formula:

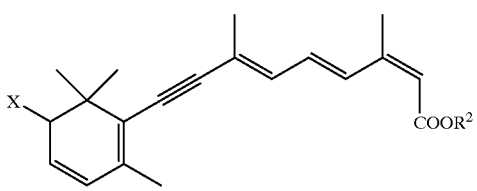

In all the above formulas, X, $R^1$ and $R^2$ are as described for formula I.

Examples of compounds of the invention are:

(2Z,4E,6E,8E)-(R)-9-(4-Hydroxy-2,6,6-trimethyl-cyclohex-1-enyl)-3,7-dimethyl-nona-2,4,6,8-tetraenoic acid, (2Z,4E,6E)-(R)-9-(4-hydroxy-2,6,6-trimethyl-cyclohex-1-enyl)-3,7-dimethyl-nona-2,4,6-trien-8-ynoic acid, ethyl (2Z,4E,6E,8E)-(R)-9-(4-hydroxy-2,6,6-trimethyl-cyclohex-1-enyl)-3,7-dimethyl-nona-2,4,6,8-tetraenoate, (2Z,4E,6E,8E)-9-(5-oxo-2,6,6-trimethyl-cyclohexa-1,3-dienyl)-3,7-dimethyl-nona-2,4,6,8-tetraenoic acid, (2Z,4E,6E,8E)-(R)-9-(4-acetoxy-2,6,6-trimethyl-cyclohex-1-enyl)-3,7-dimethyl-nona-2,4,6,8-tetraenoic acid, (2Z,4E,6E,8E)-(R)-9-(4-methoxy-2,6,6-trimethyl-cyclohex-1-enyl)-3,7-dimethyl-nona-2,4,6,8-tetraenoic acid, (2Z,4E,6E,8E)-(RS)-9-(5-hydroxy-2,6,6-trimethyl-cyclohex-1-enyl)-3,7-dimethyl-nona-2,4,6,8-tetraenoic acid, (2Z,4E,6E,8E)-(RS)-9-(5-hydroxy-2,6,6-trimethyl-cyclohexa-1,3-dienyl)-3,7-dimethyl-nona-2,4,6,8-tetraenoic acid, (2Z,4E,6E,8E)-9-(5-oxo-2,6,6-trimethyl-cyclohex-1-enyl)-3,7-dimethyl-nona-2,4,6,8-tetraenoic acid, (2Z,4E,6E,8E)-9-(4-oxo-2,6,6-trimethyl-cyclohex-1-enyl)-3,7-dimethyl-nona-2,4,6,8-tetraenoic acid, (2Z,4E,6E,8E)-(S)-9-(4-hydroxy-2,6,6-trimethyl-cyclohex-1-enyl)-3,7-dimethyl-nona-2,4,6,8-tetraenoic acid, and (2Z,4E,6E,8E)-(RS)-9-(4-hydroxy-2,6,6-trimethyl-cyclohex-1-enyl)-3,7-dimethyl-nona-2,4,6,8-tetraenoic acid.

The compounds of the invention can be manufactured by reacting a compound of the formula:

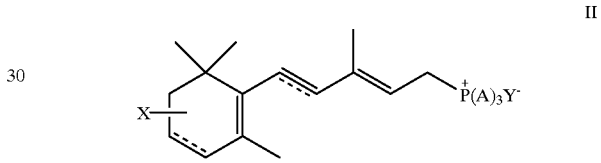

wherein A is phenyl or substituted phenyl and $Y^-$ is an anion, and X and the dotted bonds have the significance given above, with 5-hydroxy-4-methyl-5H-furan-2-one in the presence of a base, isomerizing isomers present in the reaction product in which the C=C double bond formed in the reaction has the cis-configuration to the trans isomers and, if desired, subjecting the reaction product of formula I to one or more of the following operations:

a) esterification of a carboxyl or hydroxy group;
b) etherification of a hydroxy group;
c) oxidation of a hydroxy group to an oxo group;
d) reduction of an oxo group to a hydroxy group;
e) steric inversion of a hydroxy group; and
f) conversion of a carboxy group into a salt.

The foregoing reactions for the preparation of the compounds of the invention are not critical and can be performed according to methods known per se.

The reaction of compound II can be carried out according to the known methods of the Wittig reaction. In this, the reaction partners are reacted with one another in the presence of an acid-binding agent, e.g., in the presence of a strong base such as KOH in an aqueous solvent; or sodium hydride, potassium tert.butylate or sodium ethylate in an anhydrous solvent such as dimethylformamide or methylene chloride, in a temperature range lying between about −30° C. and room temperature. Preferably, compounds of formula II in which X is oxo or hydroxy are used. The Wittig reaction yields a mixture of cis/trans isomers of the C=C double bond formed in the reaction. This mixture of 4E/Z isomers can be isomerized selectively to the 4E-isomers in a manner known per se, e.g., by treatment with Pd catalysts, such as Pd-(II) nitrate.

Of the inorganic acid anions Y⁻ the chloride and bromide ions or the hydrosulphate ion are preferred and of the inorganic acid anions the tosyloxy ion is preferred. Group A is preferably phenyl.

The esterification of a carboxyl group in a compound of formula I can be carried out, e.g., by reaction with an alkyl halide in the presence of a base such as potassium carbonate, in an organic solvent such as e.g. ethyl acetate. The esterification of a hydroxy group can be carried out by reaction with an acyl halide in the presence of a base such as pyridine. A hydroxy group can be oxidized to an oxo, e.g., according to the methods of Swern (dimethyl sulphoxide/oxalyl chloride) or Dess-Martin (periodate). The reduction of an oxo group to a hydroxy group can be carried out with hydride reducing agents such as $NaBH_4$. The steric configuration of a hydroxy group can be inverted according to the Mitsunobu method (reaction with triphenylphosphine, p-nitrobenzoic acid and diethyl azodicarboxylate and subsequent saponification).

Examples of salts into which the carboxylic acids of formula I can be converted are alkali metal salts, such as sodium and potassium salts, alkaline earth metal salts, such as calcium and magnesium salts, and ammonium salts, e.g., salts with alkylamines and hydroxyalkylamines or with other organic bases, such as dimethylamine, diethanolamine and piperidine.

The compounds of formula II can be prepared as described in *Pure and Appl. Chem.*, 57, 741 (1985) or the other literature references given therein.

The compounds in accordance with the invention can be used for the therapy and prophylaxis of dermatological disorders which are accompanied by epithelial lesions, e.g., acne and psoriasis, as well as malignant and premalignant epithelial lesions, tumours and precancerous changes of the mucous membrane in the mouth, tongue, larynx, oesophagus, bladder, cervix and colon. The preferred use of the compounds of the invention is in the treatment of acne.

The compounds of the invention can accordingly be used in the form of pharmaceutical preparations.

The preparations which are used for systemic administration can be produced by any conventional means, e.g., by adding a compound of the invention as the active ingredient to non-toxic, inert, solid or liquid carriers which are usual in such preparations.

The preparations can be administered enterally, parenterally or topically. Preparations in the form of tablets, capsules, dragées, syrups, suspensions, solutions and suppositories are suitable for enteral administration. Preparations in the form of infusion or injection solutions are suitable for parenteral administration.

For enteral and parenteral administration, the compounds of the invention are administered to adults in amounts of about 10–400 mg/day, preferably 20–200 mg/day.

For topical administration, the active ingredients are conveniently used in the form of ointments, tinctures, creams, solutions, lotions, sprays, suspensions and the like. Ointments and creams as well as solutions are preferred. These preparations adapted for topical administration can be produced by mixing the compound of the invention with non-toxic, inert, solid or liquid carriers which are suitable for topical treatment and which are usual in such preparations.

About 0.1–5%, preferably 0.3–2%, solutions as well as about 0.1–5%, preferably 0.3–2%, ointments or creams are suitable for topical administration.

If desired, an antioxidant, e.g., tocopherol, N-methyl-γ-tocopheramine as well as butylated hydroxyanisole or butylated hydroxytoluene, can be admixed with the preparations.

The activity of the compounds in accordance with the invention in the treatment of acne can be demonstrated using the test procedures described hereinafter:

1. Inhibition of the proliferation of human sebocytes (in vitro) Literature: Methods in Enzymology 190, 334 (1990), T. Doran and S. Shapiro 2. Changes in the differentiation of pig sebocytes (in vitro), induction of keratin 7.

Cultures of pig sebocytes are prepared from isolated sebum glands of conscious minipigs. They react to treatment with retinoids by expressing keratin 7, which also corresponds to the in vivo situation. Keratin 7 is considered to be a marker for a modified differentiation of sebocytes. The resulting phenotype can no longer produce sebum. The measurement of the keratin 7 induction is based on an ELISA assay using a mouse-monoclonal antikeratin 7-antibody.

3. Minipig model (in vivo)

The skin of the minipig has a similar anatomical structure to that of human skin. In particular, the sebum glands resemble those of human acne patients. Under retinoid treatment they show the same histological changes as in human beings. The pigs receive a daily oral dosage of test substance during 8 weeks. A biopsy is taken and investigated histologically every 2 weeks.

In this test the compound prepared in Example 1 shows at a dosage of 10 mg/kg already after 3–4 weeks a clear reduction in sebum glands, which have largely disappeared after 8 weeks. In contrast to isotretinoin, no side effects on skin and mucous membrane occur at a dosage of 50 mg/kg.

Teratogenic effects are the most severe side effects of all retinoids. The compounds claimed herein are significantly less teratogenic than, e.g., isotretinoin or tretinoin. The limb bud cell culture assay (Arch. Toxiol. 60, 403 [1987] A. Kistler) was used to evalute the teratogenic potential. The correlation between $IC_{50}$ in this test and the in vivo teratogenicity is very good.

| Compound of Example | $IC_{50}$ (nM) |
|---|---|
| 1 | >1000 |
| 3 | >1000 |
| 4 | >1000 |
| Isotretinoin | 200 |
| Tretinoin | 80 |

The invention is illustrated in more detail by the following Examples.

EXAMPLE 1

50 g of [(2E,4E)-(R)-5-(4-hydroxy-2,6,6-trimethyl-1-cyclohexen-1-yl)-3-methyl-2,4-pentadienyl]-triphenylphosphonium chloride were dissolved in 500 ml of isopropanol and treated with 11 g of 5-hydroxy-4-methyl-5H-furan-2-one. After cooling the reaction mixture to −30° C. 120 ml of an aqueous 2N KOH solution were added dropwise and the mixture was stirred at −30° C. under argon for a further hour. The reaction mixture was subsequently poured on to 1.3 l of ice-water, extracted 6 times with 500 ml of a hexane/ethyl acetate mixture (2:1) each time, the aqueous, alkaline solution was acidified by adding ice-cold 3N sulphuric acid while cooling with ice and subsequently extracted 3 times with ethyl acetate. The organic phase was washed with saturated sodium chloride solution, dried over sodium sulphate and evaporated. The viscous, yellow residue was again dissolved in 800 ml of ethyl acetate, treated with 100 g of silica gel (Merck 0.063–0.2 mm), warmed slightly on a steam bath for 5 minutes while stirring vigorously and, after filtration, concentrated on a rotary evaporator.

The thus-obtained yellow, crystalline crude product was treated with 500 ml of acetonitrile and heated to 50° C. under argon. A clear, yellow solution was obtained by the portionwise addition of about 700 ml of acetonitrile. After the addition of 1.1 g of triphenylphosphine and 118 ml of a 0.125% solution of palladium(II) nitrate in acetonitrile the reaction mixture was stirred at 50° C. for 3 hours. The end product crystallized out upon cooling the reaction solution to −10° C. It was filtered off, washed with hexane and dried at 40° C. in a high vacuum. Recrystallization from hexane/ethyl acetate gave 15 g of (2Z,4E,6E,8E)-(R)-9-(4-hydroxy-2,6,6-trimethyl-cyclohex-1-enyl)-3,7-dimethyl-nona-2,4,6,8-tetraenoic acid, m.p. 180–182° C. (dec.), $[\alpha]_D^{20}$=−49.7 (c=1, dioxan).

EXAMPLE 2

3 g of the carboxylic acid obtained according to Example 1 were treated in succession with 120 ml of methyl ethyl ketone, 5.2 g of finely ground potassium carbonate and 7.4 g of ethyl iodide and heated at reflux under argon and while stirring vigorously for 2.5 hours. The reaction mixture was poured on to ice/1N hydrochloric acid, extracted with ether, washed with water, dried and evaporated. The oily crude product was filtered over silica gel (eluent hexane/ethyl acetate 2:1) and recrystallized from hexane. There were obtained 2.9 g of ethyl (2Z,4E,6E, 8E)-(R)-9-(4-hydroxy-2,6,6-trimethyl-cyclohex-1-enyl)-3,7-dimethyl-nona-2,4,6,8-tetraenoate in yellow crystals, m.p. 93–95° C., $[\alpha]_D^{20}$=−45.5 (c=1, dioxan).

EXAMPLE 3

In analogy to Example 1, by reacting 10 g of [(E)-(R)-5-(4-hydroxy-2,6,6-trimethyl-1-cyclohexen-1-yl)-3-methyl-2-penten-4-ynyl]-triphenylphosphonium chloride with 2.3 g of 5-hydroxy-4-methyl-5H-furan-2-one there were obtained, after palladium-catalyzed isomerization of the crude product and recrystallization from hexane/ethyl acetate, 3.1 g of (2Z,4E,6E)-(R)-9-(4-hydroxy-2,6,6-trimethyl-cyclohex-1-enyl)-3,7-dimethyl-nona-2,4,6-trien-8-ynoic acid as yellow crystals, m.p. 189–190° C. (dec.), $[\alpha]_D^{20}$=−87.3 (c=1, CHCl$_3$).

EXAMPLE 4

9 g of [(2E,4E)-3-methyl-5-(2,6,6-trimethyl-5-oxo-1,3-cyclohexadien-1-yl)-2,4-pentadienyl] triphenylphosphonium bromide and 1.7 g of 5-hydroxy-4-methyl-5H-furan-2-one were suspended in 100 ml of isopropanol. After cooling the reaction mixture to −30° C. 20 ml of an aqueous 2N potassium hydroxide solution were added dropwise. After stirring at −30° C. for 30 minutes the reaction mixture was poured on to ice-water, extracted 3 times with hexane, the alkaline aqueous phase was acidified with ice-cold 3N sulphuric acid and extracted several times with ethyl acetate. The organic phase was washed with water, dried and evaporated.

The brownish, viscous oil was purified by chromatography on silica gel (eluent hexane/ethyl acetate 3:1). The thus-obtained yellow oil (about 4 g) was dissolved in 100 ml of acetonitrile, treated with 150 mg of triphenylphosphine and, after heating to 50° C., 10 ml of a 0.125% palladium(II) nitrate solution in acetonitrile were added dropwise. After heating to 50° C. for 2 hours the reaction mixture was cooled to 0° C. After 2 hours the separated crystals were filtered off under suction and recrystallized from hexane/ethyl acetate. There were obtained 1.4 g of (2Z,4E,6E,8E)-9-(5-oxo-2,6,6-trimethyl-cyclohexa-1,3-dienyl)-3,7-dimethyl-nona-2,4,6,8-tetraenoic acid in yellow crystals, m.p. 188° C. (dec.).

EXAMPLE 5

7 g of [(2E,4E)-3-methyl-5-(2,6,6-trimethyl-5-oxo-1-cyclohexen-1-yl)-2,4-pentadienyl]triphenylphosphonium bromide and 1.4 g of 5-hydroxy-4-methyl-5H-furan-2-one were suspended in 100 ml of isopropanol. After cooling the reaction mixture to −30° C. a solution of 1.76 g of potassium hydroxide in 30 ml of isopropanol was added dropwise thereto. After stirring at −30° C. for 40 minutes the reaction mixture was poured on to 200 ml of ice-water, extracted 6 times with a hexane/ethyl acetate mixture (2:1), the organic phases were washed with water, the combined, aqueous phases were acidified with 3N sulphuric acid and extracted several times with ethyl acetate. The organic phases were washed (H$_2$O), dried (Na$_2$SO$_4$) and evaporated.

The oily residue was dissolved in 100 ml of ethyl acetate, treated with 12 g of silica gel and stirred vigorously at 40° C. under argon.

After cooling the silica gel was filtered off, rinsed well with ethyl acetate and the solution was evaporated. The residue was dissolved in 30 ml of acetonitrile and, after the addition of 256 mg of triphenylphosphine, treated dropwise at 50° C. with a solution of 26 mg of palladium nitrate in 5 ml of acetonitrile. After stirring at 50° C. for 1 hour the reaction mixture was cooled to 0° C. and, after 1 hour, the precipitate which separated was filtered off. After recrystallization twice from hexane/ethyl acetate there were obtained 1.4 g of (2Z,4E,6E,8E)-3,7-dimethyl-9-(2,6,6-trimethyl-5-oxo-cyclohex-1-enyl)-nona-2,4,6,8-tetraenoic acid in yellow crystals, m.p. 178–179° C.

EXAMPLE 6

0.5 g of (2Z,4E,6E,8E)-3,7-dimethyl-9-(2,6,6-trimethyl-5-oxo-cyclohex-1-enyl)-nona-2,4,6,8-tetraenoic acid was dissolved in 25 ml of ethanol while warming slightly and treated with 100 mg of sodium borohydride while cooling with ice. After stirring at 0° C. for 1 hour the reaction mixture was poured on to ice-water, acidified with 2N hydrochloric acid and extracted with ethyl acetate. The organic phases were washed (H$_2$O), dried (Na$_2$SO$_4$) and evaporated. The amorphous residue was filtered over a small column (silica gel, hexane/ethyl acetate=1:1) and recrystallized from hexane/ethyl acetate. 0.35 g of (2Z,4E,6E,8E)-9-(5-hydroxy-2,6,6-trimethyl-cyclohex-1-enyl)-3,7-dimethyl-nona-2,4,6,8-tetraenoic acid was obtained in yellow crystals, m.p. 152–154° C.

EXAMPLE 7

2.5 g of the ethyl ester prepared according to Example 2 were dissolved in 35 ml of abs. tetrahydrofuran and treated in succession at 0° C. with 3.8 g of triphenylphosphine, 2.4 g of p-nitrobenzoic acid and dropwise with a solution of 2.5 g of diethyl azodicarboxylate in 30 ml of tetrahydrofuran. After stirring at room temperature for 2 hours the mixture was evaporated, the residue was taken up with ether and stored in a refrigerator for 3 hours. The precipitate (triphenylphosphine oxide) which thereby separated was removed, the filtrate was concentrated and the residue was purified by chromatography (silica gel, hexane/ethyl acetate 5%).

There was obtained 0.68 g of a yellow oil which was dissolved in 15 ml of ethanol and, after the addition of a solution of 0.78 g of potassium hydroxide in 3 ml of water, 3 ml of ethanol and 3 ml of tetrahyrofuran, stirred at 45° C. for 6 hours. The reaction mixture was subsequently poured on to ice-water, acidified with 1N hydrochloric acid and extracted with ethyl acetate. The organic phase was washed ($H_2O$), dried ($Na_2SO_4$) and evaporated. The crystalline residue was filtered over a small column (silica gel, ethyl acetate) and, after recrystallization from hexane/ethyl acetate, gave 190 mg of (2Z,4E,6E,8E)-(S)-9-(4-hydroxy-2,6,6-trimethyl-cyclohex-1-enyl)-3,7-dimethyl-nona-2,4,6,8-tetraenoic acid in yellow crystals, m.p. 178–180° C., $[\alpha]_D^{20}$=+48.2 (c=0.66, dioxan).

EXAMPLE 8

1 g of the carboxylic acid prepared according to Example 4 was suspended in 50 ml of methyl ethyl ketone, treated with 1.5 g of finely ground potassium carbonate and 1.3 ml of ethyl iodide and heated at reflux for 1 hour. The cooled reaction mixture was poured on to ice-water, neutralized with 1N hydrochloric acid, extracted with ethyl acetate, washed ($H_2O$), dried ($Na_2SO_4$) and evaporated. The thus-obtained yellow oil was purified by chromatography (silica gel, hexane/ethyl acetate=2:1) and gave 1.5 g of the corresponding ethyl ester as a yellow oil.

1.18 g of cerium trichloride•$7H_2O$ were dissolved in 25 ml of methanol and treated in succession with a solution of the above ethyl ester in 5 ml of methanol and 120 mg of sodium borohydride. After the evolution of gas had ceased (about 5 minutes) the mixture was evaporated and the orange residue was purified by chromatography (silica gel, hexane/ethyl acetate=4:1). 1.04 g of the corresponding hydroxyester were obtained as a yellow oil. This oil was dissolved in 25 ml of ethanol, treated with a solution of 1.6 g of potassium hydroxide in 12 ml of water and stirred at 40° C. for 4 hours under argon. The cooled reaction mixture was poured on to ice-water, acidified to pH 3 with 1N hydrochloric acid and extracted with ethyl acetate. The organic phase was washed ($H_2O$), dried ($Na_2SO_4$) and evaporated and gave 0.95 g of an orange, amorphous residue. Filtration over a small column (silica gel, hexane/ethyl acetate=1:1) and crystallization from hexane/ethyl acetate gave (2Z,4E,6E,8E)-9-(5-hydroxy-2,6,6-trimethyl-cyclohex-1,3-dienyl)-3,7-dimethyl-nona-2,4,6,8-tetraenoic acid in yellow-orange crystals, m.p. 108–110° C.

EXAMPLE A

Hard gelatine capsules can be produced as follows:

| Ingredient | mg/capsule |
| --- | --- |
| 1. Spray-dried powder containing 75% compound I | 20 |
| 2. Sodium dioctylsulphosuccinate | 0.2 |
| 3. Sodium carboxymethylcellulose | 4.8 |
| 4. Microcrystalline cellulose | 86.0 |
| 5. Talc | 8.0 |
| 6. Magnesium stearate | 1.0 |
| Total | 120 |

The spray-dried powder, which is based on the active ingredient, gelatine and microcrystalline cellulose and which has an average active ingredient particle size of <1 μm (measured by means of autocorrelation spectroscopy), is moistened with an aqueous solution of sodium carboxymethylcellulose and sodium dioctylsulphosuccinate and kneaded. The resulting mass is granulated, dried and sieved, and the granulate obtained is mixed with microcrystalline cellulose, talc and magnesium stearate. The powder is filled into size 0 capsules.

EXAMPLE B

Tablets can be produced as follows:

| Ingredient | mg/tablet |
| --- | --- |
| 1. Compound I as a finely milled powder | 20 |
| 2. Powd. lactose | 100 |
| 3. White corn starch | 60 |
| 4. Povidone K30 | 8 |
| 5. White corn starch | 112 |
| 6. Talc | 16 |
| 7. Magnesium stearate | 4 |
| Total | 320 |

The finely milled substance is mixed with lactose and a portion of the corn starch. The mixture is moistened with an aqueous solution of Povidone K30 and kneaded, and the resulting mass is granulated, dried and sieved. The granulate is mixed with the remaining corn starch, talc and magnesium stearate and pressed to tablets of suitable size.

EXAMPLE C

A lotion can be produced as follows:

| Ingredient | |
| --- | --- |
| 1. Compound I, finely milled | 1.0 g |
| 2. Carbopol 934 | 0.6 g |
| 3. Sodium hydroxide | q.s. ad pH 6 |
| 4. Ethanol, 94% | 50.0 g |
| 5. Demineralised water | ad 100.0 g |

The active ingredient is incorporated in the 94% ethanol/water mixture with protection from light. Carbopol 934 is stirred in until gelling is complete and the pH value is adjusted with sodium hydroxide.

EXAMPLE D

A cream can be produced in a manner known per se from the ingredients listed hereinafter:

| | Wt. % |
| --- | --- |
| Compound of formula I | 0.1–5 |
| Cetyl alcohol | 5.25–8.75 |
| Arlacel 165 (glyceryl/PEG 100 stearate) | 3.75–6.25 |
| Miglyol 818 (caprylic/capric/linoleic acid triglyceride) | 11.25–18.75 |
| Sorbitol solution | 3.75–6.25 |
| EDTA $Na_2$ | 0.075–0.125 |
| Carbopol 934P (carbomer 934P) | 0.15–0.25 |
| Butylated hydroxyanisole | 0.0375–0.0625 |
| Methylparaben | 0.135–0.225 |
| Propylparaben | 0.0375–0.0625 |
| NaOH (10% solution) | 0.15–0.25 |
| Water q.s. | 100.00 |

EXAMPLE E

|  | Wt. % |
|---|---|
| Compound of formula I | 0.1–5 |
| Pluronic L 101 (poloxamer 331) | 10.00 |
| Aerosil 200 (silicon dioxide) | 8.00 |
| PCL liquid (fatty acid ester | 15.00 |
| Cetiol V (decyl oleate) | 20.00 |
| Neobee oil (medium chain triglyceride) | 15.00 |
| Euhanol G (octyldodecanol), q.s. | 100.00 |

The physical properties of the preparation can be altered by varying the ratio between the adjuvants in Examples D and E.

We claim:

1. The geometric isomer (2Z,4E,6E,8E)-(R)-9-(4-hydroxy-2,6,6-trimethyl-cyclohex-1-enyl)-3,7-dimethyl-nona-2,4,6,8-tetraenoic acid substantially free of the other geometric isomers.

2. The geometric isomer ethyl (2Z,4E,6E,8E)-(R)-9-(4-hydroxy-2,6,6-trimethyl-cyclohex-1-enyl)-3,7-dimethyl-nona-2,4,6,8-tetraenoate substantially free of the other geometric isomers.

3. The geometric isomer (2Z,4E,6E,8E)-(R)-9-(4-acetoxy-2,6,6-trimethyl-cyclohex-1-enyl)-3,7-dimethyl-nona-2,4,6,8-tetraenoic acid substantially free of the other geometric isomers.

4. The geometric isomer (2Z,4E,6E,8E)-(R)-9-(4-methoxy-2,6,6-trimethyl-cyclohex-1-enyl)-3,7-dimethyl-nona-2,4,6,8-tetraenoic acid substantially free of the other geometric isomers.

5. The geometric isomer (2Z,4E,6E,8E)-(S)-9-(4-hydroxy-2,6,6-trimethyl-cyclohex-1-enyl)-3,7-dimethyl-nona-2,4,6,8-tetraenoic acid substantially free of the other geometric isomers.

6. The compound having the formula:

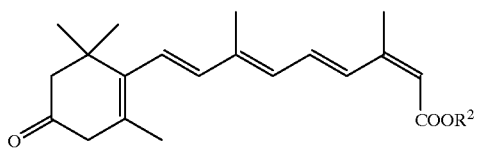

wherein $R^2$ is is hydrogen or alkyl.

7. The compound of claim 6 wherein said compound is (2Z,4E,6E,8E)-9-(4-oxo-2,6,6-trimethyl-cyclohex-1-enyl)-3,7-dimethyl-nona-2,4,6,8-tetraenoic acid.

8. The compound (2Z,4E,6E,8E)-9-(5-hydroxy-2,6,6-trimethyl-cyclohex-1-enyl)-3,7-dimethyl-nona-2,4,6,8-tetraenoic acid.

9. A compound having the formula:

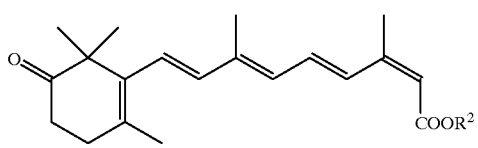

wherein $R^2$ is hydrogen or alkyl.

10. The compound of claim 9 wherein said compound is (2Z,4E,6E,8E)-3,7-Dimethyl-9-(2,6,6-trimethyl-5-oxo-cyclohex-1-enyl)-nona-2,4,6,8-tetraenoic acid.

11. The compound is (2Z,4E,6E,8E)-9-(5-hydroxy-2,6,6-trimethyl-cyclohex-1,3-dienyl)-3,7-dimethyl-nona-2,4,6,8-tetraenoic acid.

12. A compound having the formula:

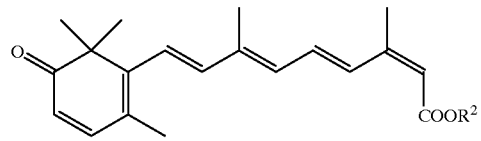

wherein $R^2$ is hydrogen or alkyl.

13. The compound of claim 12 wherein said compound is (2Z,4E,6E,8E)-9-(5-oxo-2,6,6-trimethyl-cyclohexa-1,3-dienyl)-3,7-dimethyl-nona-2,4,6,8-tetraenoic acid.

14. The compound having the formula

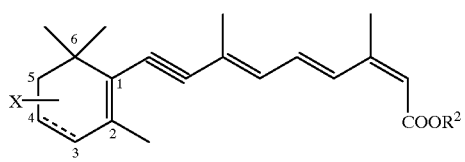

wherein $R^2$ is hydrogen or alkyl and X is oxo or a group $OR^1$ in the 4- or 5-position; and $R^1$ is hydrogen, alkyl, or acyl.

15. The compound of claim 14 having the formula:

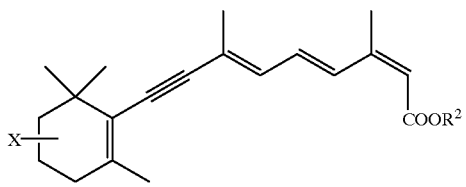

wherein X and $R^2$ are as in claim 14.

16. The compound of claim 15 having the formula:

IG

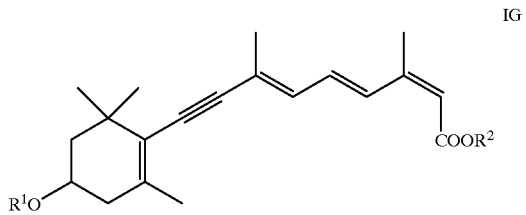

wherein $R^1$ and $R^2$ are as in claim 14.

17. The compound of claim 16 wherein said compound is (2Z,4E,6E)-(R)-9-(4-Hydroxy-2,6,6-trimethyl-cyclohex-1-enyl)-3,7-dimethyl-nona-2,4,6-trien-8-ynoic acid.

18. The compound of claim 14 having the formula:

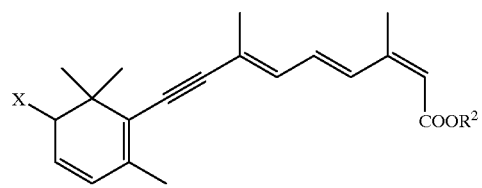

wherein X and $R^2$ are as in claim 14.

* * * * *